United States Patent [19]

Fuller, Jr. et al.

[11] Patent Number: 5,177,245
[45] Date of Patent: Jan. 5, 1993

[54] PROCESS FOR PREPARING CYCLOHEXENYLHYDROQUINONE

[75] Inventors: Dewey W. Fuller, Jr., Bristol; Gether Irick, Jr., Gray, both of Tenn.

[73] Assignee: Eastman Kodak Company, Rochester, N.Y.

[21] Appl. No.: 797,659

[22] Filed: Nov. 25, 1991

[51] Int. Cl.⁵ .................... C07C 69/76; C07C 63/66; C07C 65/105; C07C 41/06
[52] U.S. Cl. ........................................ 560/55; 560/56; 560/102; 560/129; 562/469; 562/492; 568/631; 568/644; 568/667; 568/670; 568/743; 568/807; 585/25; 585/400; 585/425
[58] Field of Search .............. 568/743, 644, 670, 667, 568/631, 641, 644, 807; 562/492, 469; 560/129, 102, 55, 56; 585/25, 425, 400

[56] References Cited

FOREIGN PATENT DOCUMENTS 925819  5/1963  United Kingdom ................ 568/743
1073638 6/1967  United Kingdom ................ 568/743

OTHER PUBLICATIONS

March, *Advanced Organic Chemistry*, pp. 789–780, 1985.
McOmie, *Protective Groups In Organic Chemistry*, pp. 327–328, 337–338, 1973.
D. A. Pisanenko and S. A. Nesterenko, *Zh. Org. Khim.*, 15(9), 1979; "Alkenylation of Resorcinol and Hydroquinone Monomethyl Ethers with 1,3-cyclodienes".

*Primary Examiner*—Marianne M. Cintins
*Assistant Examiner*—Margaret Page
*Attorney, Agent, or Firm*—Bernard J. Graves, Jr.; William P. Heath, Jr.

[57] ABSTRACT

Provided is a process for preparing optionally-substituted cyclohexenylhydroquinones starting from cyclohexanone.

10 Claims, No Drawings

PROCESS FOR PREPARING CYCLOHEXENYLHYDROQUINONE

FIELD OF THE INVENTION

This invention belongs to the field of organic chemistry. More particularly, this invention relates to a process for preparing cyclohexenylhydroquinone.

BACKGROUND OF THE INVENTION

Aryl substituted monomers are useful in making liquid crystal polymers. Phenylhydroquinone, an example of one of these commercially useful monomers, can be prepared by alkylation of hydroquinone with cyclohexene, followed by dehydrogenation of the resulting cyclohexylhydroquinone over a noble metal catalyst at high temperatures. A considerable problem with this route is large yield losses which occur because of product and substrate decomposition under the severe conditions needed for the dehydrogenation of a saturated ring. Alternatively, cyclohexenylhydroquinone can be dehydrogenated under milder conditions which do not give large amounts of decomposition products.

D. A. Pisanenko and S. A. Nesterenko, Zh. Org. Khim. 15(9), 1979, describe the alkylation of hydroquinone with 1,3 cyclohexadiene using phosphoric acid catalyst to give cyclohexenylhydroquinone. This preparative method is severely limited by the tendency for 1,3 cyclohexadiene to react with itself in a disproportionation reaction to give benzene and cyclohexene. The cyclohexene thus formed then reacts with hydroquinone to give cyclohexyl hydroquinone rather than the desired cyclohexenylhydroquinone or, alternatively, reacts with another mole of cyclohexadiene to give benzene and cyclohexane. In addition, cyclohexadienes are expensive and availability is limited.

SUMMARY OF THE INVENTION

The present invention provides a process for preparing optionally substituted cyclohexenylhydroquinones starting from cyclohexanone, followed by formation of a ketal, followed by dehydration to provide a 1 alkoxycyclohexenyl intermediate. This intermediate can then be utilized in an alkylation reaction with di(alkyl, hydroxy, or alkoxy) benzene to provide cyclohexenylhydroquinones and other cyclohexenylbenzene compounds.

DETAILED DESCRIPTION OF THE INVENTION

The present invention provides a process for preparing a compound of Formula (I).

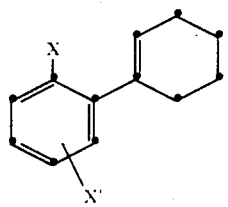

(I)

wherein x and x' are independently R, —OH, —OR, —COOH, or —COOR, wherein R is $C_1$–$C_{10}$ alkyl, with the proviso that if one of x or x' is —COOH or —COOR, then the other of x or x' is R, —OH, or —OR, which comprises the steps:

(a) treating cyclohexanone with a compound of the formula R-OH in the presence of an acid catalyst to form a compound of the formula

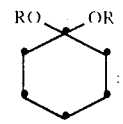

followed by
(b) heating to provide a compound of the formula

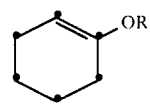

followed by
(c) treatment with a compound of the formula

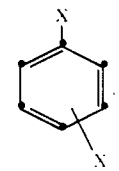

in the presence of an acid catalyst, wherein x and x' are as defined above.

In this process, it is noted that if one of x or x' is —COOH or —COOR, then the other of x or x' is R, —OH, or —OR. This proviso is present because it is believed that the presence of two ester or acid groups would render the substrate unreactive.

As a further aspect of this invention, there is provided a process for preparing compounds of Formula (I) which comprises reaction of the product of step (b) above with a compound as set forth in step (c) above.

The term "$C_1$–$C_{10}$ alkyl" refers to straight or branched chain hydrocarbon groups comprised of from one to ten carbon atoms.

In this process cyclohexanone can be treated with an excess of alcohol such as methanol in the presence of an acid catalyst to generate dialkylketals such as 1,1-dimethylcyclohexane. Ketals can be generated without the use of a catalyst, but the preferred method involves use of an acid catalyst.

The reactions are preferably conducted at temperatures in the range of about 20° to about 170° C.; further preferred temperatures are about 10 to about 70° C. A wide range of Lewis and Bronsted acid catalysts may be used. Exemplary catalysts include:

| | |
|---|---|
| acetic acid, | phosphoric acid, |
| sulfuric acid, | methanesulfonic acid, |
| trifluoromethanesulfonic acid, | polyphosphoric acid, |
| acidic molecular sieves, | trichloracetic acid, |
| p-toluenesulfonic acid, | trifluoroacetic acid, |
| dichloroacetic acid, | |
| aluminum trichloride, | |
| aluminum tribromide, | |
| boron trifluoride, and | |
| acidic polymeric resins, such as, for example, AMBERLYST ® 15 | |
| acidic metal oxides, such as, for example, $SiO_2/Al_2O_3$, and | |

-continued molecular sieves

Preferred for ease of handling, workup, etc., are the solid acids such as AMBERLYST®15, AEROCAT®, amorphous silica aluminates, and zeolite catalysts. Another advantage with these catalysts is that they are non-corrosive and may be recycled.

Water generated during the preparation of the ketal is preferably removed. Removal of water is desirable since this shifts the equilibrium to favor formation of the ketal and the alkyloxycyclohexene. It is readily removed from the reaction mixture by well known azeotropic procedures using solvents such as chloroform, benzene, toluene and the like. Removal of water in the diethoxyketal reaction can be accomplished by distilling over ethanol/water azeotrope. Also, molecular sieves can be added to facilitate water removal.

The next step in the process involves cracking of the ketal to provide alkyloxylcyclohexene while liberating alcohol. One facile process to accomplish this result involves simultaneous cracking of ketal and distillation of the resulting alkyloxycyclohexene in the presence of an acid catalyst. At higher distillation temperatures, thermal cracking occurs without a catalyst. Typically useful cracking temperatures include about $25°$ C. to about $260°$ C.

The alkyloxycyclohexenes are excellent alkylating agents. For example, hydroquinone is readily alkylated by methoxycyclohexene in the presence of an acid catalyst to provide cyclohexenylhydroquinone. Useful temperature ranges include about $80°$ C. to about $260°$ C. but temperatures of about $125°$ C. to about $170°$ C. are preferred. Alcohol is liberated during the alkylation reaction. Again, a wide range of acid catalysts are useful and typical ones include those listed above. The medium and large pore zeolites are preferred catalysts for this reaction.

EXPERIMENTAL SECTION

Example 1

Preparation of 1,1-Dimethoxycyclohexane

| Materials: | 60 milliliters methanol |
| --- | --- |
| | 9.5 grams cyclohexanone |
| | 1.0 gram glacial acetic acid |

Method: Charged all materials to a round bottom flask and stirred at reflux 4 hours.

| GLC Analysis (Methanol not reported) | |
| --- | --- |
| Cyclohexanone | 34.49% |
| 1,1-Dimethoxycyclohexane | 63.65% |
| Methoxycyclohexene | 1.86% |

Example 2

Preparation of 1,1-Dimethoxycyclohexane

| Materials: | 60 milliliters methanol |
| --- | --- |
| | 9.5 grams cyclohexanone |
| | 1.0 gram Amberlyst 15 resin |

Method: Charged all materials to a round bottom flask and stirred at reflux 4 hours.

| GLC Analysis (Methanol not reported) | |
| --- | --- |
| Cyclohexanone | 28.75% |
| 1,1-Dimethoxycyclohexane | 68.25% |
| Methoxycyclohexene | 2.79% |

Example 3

Preparation of 1,1-Dimethoxycyclohexane

Molecular sieve was used in this example to remove water and shift the equilibrium to favor formation of the ketal and methoxycyclohexene. Also, the reaction was carried out at room temperature instead of at reflux.

| Materials: | 130 grams methanol |
| --- | --- |
| | 23 grams cyclohexanone |
| | 2.25 grams AMBERLYST 15 Resin |
| | 65 grams 3A molecular sieve (dried in argon stream for 8 hours at 400° C. before using) |

Method: Stirred in a round bottom flask at $25°$ C. for 2 hours.

| GLC Analysis (Methanol not reported) | |
| --- | --- |
| Cyclohexanone | 6.53% |
| 1,1-Dimethoxycyclohexane | 53.70% |
| Methoxycyclohexene | 36.46% |

Example 4

Preparation of 1,1-Diethoxycyclohexane

| Materials: | 270 grams Ethanol |
| --- | --- |
| | 100 grams Cyclohexanone |
| | 3.25 grams $SiO_2Al_2O_3$ DAVISON Grade 980.25 |

Method: Stirred at reflux 2.5 hours. Distilled off ethanol to azeotrope water out of the reaction. Added ethanol back to the reaction as needed. A total of 625 grams of additional ethanol added. A total of 603 grams of distillate collected.

| GLC Analysis (Ethanol not reported) | |
| --- | --- |
| Cyclohexanone | 57.49% |
| 1,1-Diethoxycyclohexane | 12.78% |
| Ethoxycyclohexene | 28.89% |

Example 5

Preparation of 1-Methoxycyclohexene

Mixtures of 1,1-dimethoxycyclohexane and methoxycyclohexene can be distilled at atmospheric pressure with a head temperature of around $145°$ C. to give a distillate which is mostly methoxycyclohexene the desired alkylating reagent. Mixtures prepared by the method described in example 2 were distilled at atmospheric pressure to give distillate with the following composition:

| GLC Analysis | |
|---|---|
| Cyclohexanone | 29.54% |
| 1,1-Dimethoxycyclohexane | 3.19% |
| 1-Methoxycyclohexene | 66.95% |

Example 6

Alkylation of Hydroquinone with Methoxycyclohexene

| Materials: | 3 grams 67% Methoxycyclohexene |
|---|---|
| | 2.5 grams Hydroquinone |
| | 20 grams Diphenylether (solvent) |
| | 1 gram SiO$_2$Al$_2$O$_3$ DAVISON Grade 970-08 |

Method: Charged the hydroquinone, diphenylether, and SiO$_2$Al$_2$O$_3$ to a round bottom flask and heated with stirring to 125° C. Added the 1-methoxycyclohexene over approximately three minutes. Stirred 20 minutes at 125° C. and sampled.

| GLC Analysis (solvent not reported) | |
|---|---|
| Methanol | 1.29% |
| 1-Methoxycyclohexene | 3.26% |
| Cyclohexanone | 19.66% |
| 1,1-Dimethoxycyclohexane | 7.17% |
| Hydroquinone | 37.39% |
| Cyclohexanone Dimers | 10.66% |
| Cyclohexenylhydroquinone | 9.17% |
| Cyclohexanone Trimers | 5.34% |

Example 7

Alkylation of Hydroquinone with 1-Methoxycyclohexene

In an effort to eliminate water, this reaction was done using dried catalyst. Water promotes formation of the hemiketal which in turn converts readily to cyclohexanone. In an acidic environment, cyclohexanone forms a dimer which dehydrates to give more water which can in turn react to form more hemiketal.

| Materials: | 3 grams 67% 1-Methoxycyclohexene |
|---|---|
| | 2.5 grams Hydroquinone |
| | 20 grams Diphenylether (solvent) |
| | 1 gram SiO$_2$Al$_2$O$_3$ DAVISON grade 970-08 (Just prior to being used, this catalyst was dried at 270° C. for 3 hours) |

Method: As per example 6.

| GLC Analysis (solvent not reported) | |
|---|---|
| Methanol | 0.61% |
| 1-Methoxycyclohexene | 14.61% |
| Cyclohexanone | 22.97% |
| 1,1-Dimethoxycyclohexane | 12.35% |
| Hydroquinone | 36.79% |
| Cyclohexanone Dimers | 1.59% |
| Cyclohexenylhydroquinone | 8.90% |
| Cyclohexanone Trimers | trace |

We claim:

1. A process for preparing a compound of Formula (I)

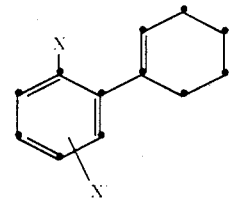

(I)

wherein x and x' are independently R, —OH, —OR, —COOOH, or —COOR, wherein R is C$_1$-C$_{10}$ alkyl, with the proviso that if one of x or x' is —COOH or —COOR, then the other of x or x' is R, —OH, or —OR, which comprises the steps:

(a) treating cyclohexanone with a compound of the formula R OH to form a compound of the formula

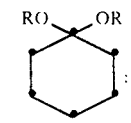

followed by
(b) heating to provide a compound of the formula

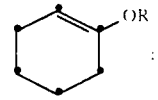

followed by
(c) treatment with a compound of the formula

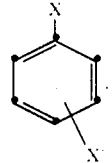

in the presence of an acid catalyst, wherein x and x' are as defined above.

2. The process of claim 1, wherein x and x' are R.
3. The process of claim 2, wherein R is methyl.
4. The process of claim 1, wherein x is —OH.
5. The process of claim 1, wherein step (a) is conducted in the presence of an acid catalyst.
6. A process for preparing a compound of Formula (I)

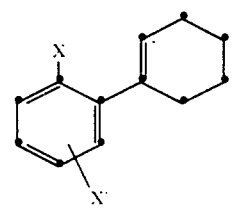

(I)

wherein x and x' are independently R, —OH, —OR, —COOH, or —COOR, wherein R is C$_1$-C$_{10}$ alkyl, with the proviso that if one of x or x' is —COOH or —COOR, then the other of x or x' is R, —OH, or —OR, which comprises treatment of a compound of the formula
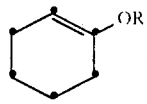
with a compound of the formula
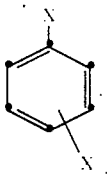
in the presence of an acid catalyst, wherein x and x' are as defined above.
7. The process of claim 6, wherein x and x' are R.
8. The process of claim 7, wherein R is methyl.
9. The process of claim 6, wherein x and x' are —OH and x' is para to x.
10. The process of claim 6, wherein x and x' are —OR.
* * * * *